(12) United States Patent
Schär et al.

(10) Patent No.: US 6,663,388 B1
(45) Date of Patent: Dec. 16, 2003

(54) CONNECTION BETWEEN A DENTAL IMPLANT AND AN ABUTMENT

(75) Inventors: Alex Schär, Riehen (CH); Vincenzo Grande, Möhlin (CH); Ulrich Mundwiler, Tenniken (CH)

(73) Assignee: Institut Straumann AG, Waldenburg (CH)

( * ) Notice: Subject to any disclaimer, the term of this patent is extended or adjusted under 35 U.S.C. 154(b) by 0 days.

(21) Appl. No.: 09/869,005

(22) PCT Filed: Dec. 27, 1999

(86) PCT No.: PCT/CH99/00628

§ 371 (c)(1),
(2), (4) Date: Sep. 17, 2001

(87) PCT Pub. No.: WO00/38588

PCT Pub. Date: Jul. 6, 2000

(30) Foreign Application Priority Data

Dec. 28, 1998 (WO) .............................. PCT/CH98/00555

(51) Int. Cl.[7] .................................................. A61C 8/00
(52) U.S. Cl. ....................................................... 433/173
(58) Field of Search ................................. 433/172, 173, 433/174, 175, 176

(56) References Cited

U.S. PATENT DOCUMENTS

| 4,246,811 A | 1/1981 | Bondhus et al. ............... 81/436 |
| 4,960,381 A | 10/1990 | Niznick ....................... 433/174 |
| 5,116,225 A | 5/1992 | Riera ......................... 433/173 |
| 5,302,126 A | 4/1994 | Wimmer et al. ............. 433/173 |
| 5,322,443 A | 6/1994 | Beaty ......................... 433/141 |
| 5,334,024 A | 8/1994 | Niznick ....................... 433/173 |
| 5,368,483 A | 11/1994 | Sutter et al. ................. 433/173 |
| 5,620,323 A | * 4/1997 | Bressman et al. .......... 433/174 |
| 5,733,122 A | 3/1998 | Gordon ....................... 433/172 |
| 5,947,733 A | 9/1999 | Sutter et al. ................. 433/173 |

FOREIGN PATENT DOCUMENTS

| DE | 9417182 | 2/1995 |
| WO | 9409717 | 5/1994 |
| WO | 9714371 | 4/1997 |

OTHER PUBLICATIONS

Schroeder, A., et al., Oral Implantology, Georg Thieme Verlag Stuttgart, New York, Second, revised edition 1996, p. 127.

* cited by examiner

Primary Examiner—John J. Wilson
(74) Attorney, Agent, or Firm—McCarter & English, LLP

(57) ABSTRACT

The invention relates to a connection between a known dental implant (1) and a straight or angular abutment (2) which can be established by means of a base screw (3) and a support ring (4). The support ring (4) is fixedly introduced into the inlet of the abutment (2) near the lower edge of same, preferably by welding or by bending over of the lower edge of the abutment (2). Before insertion of the support ring (4) the base screw (3) is introduced head first into the inlet (24) from the side of the root part of the abutment. The base screw is held in the abutment (2) by the support ring (4) on which the base screw (3) rests. The threaded shank (32) of the base screw (3) engages the inner thread (14) provided for in the implant (1) and draws the abutment (2) into the receiving hole (12) of the implant (1). An angled surface of the base screw (3) and a beveled surface of the support ring (4) contact each other so that the welding seam or bent over lower edge of the abutment (2) are relieved of axial stress. The above connection system is designed especially for implants (1) with a conical receiving hole (12) and internal polygon as well as abutments (2) having a complementary external conical shape and external polygon.

50 Claims, 8 Drawing Sheets

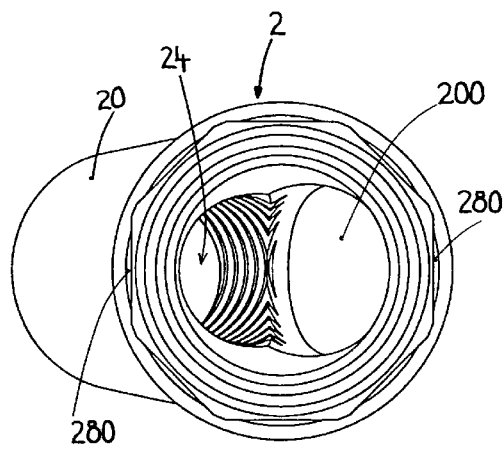
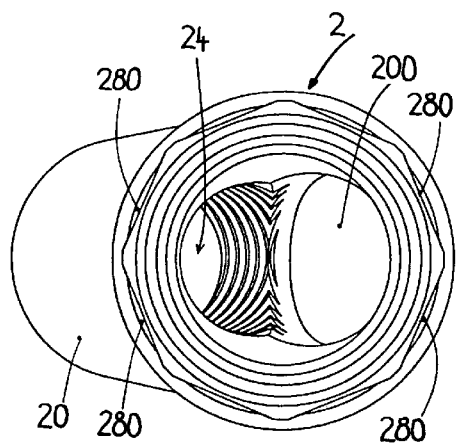
Fig. 2C    Fig. 2D
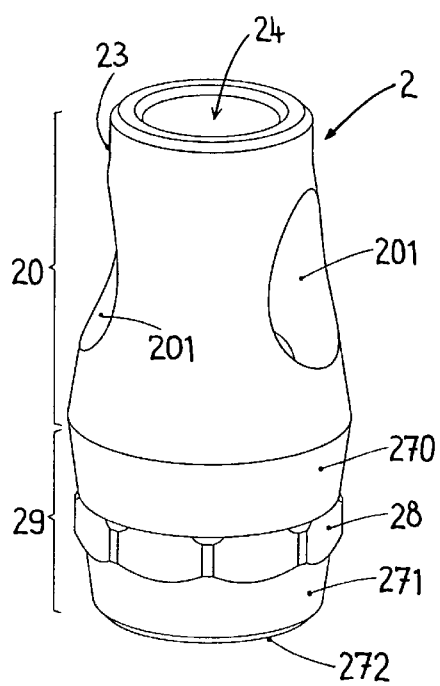
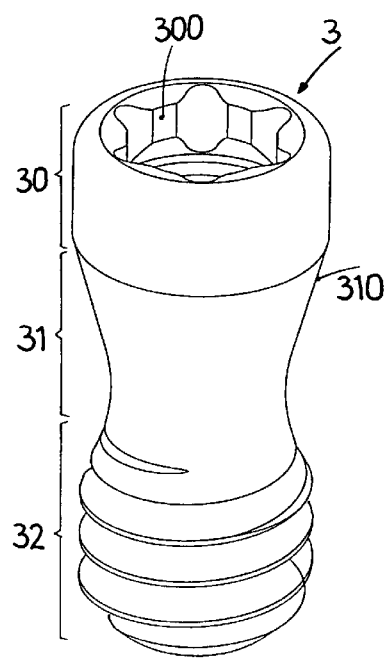
Fig. 2E    Fig. 3A

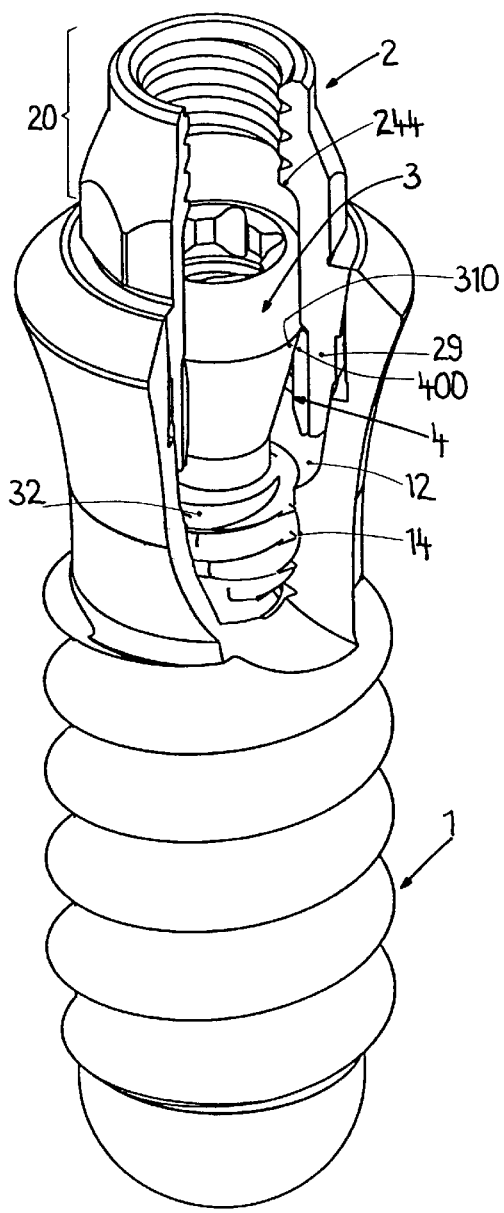
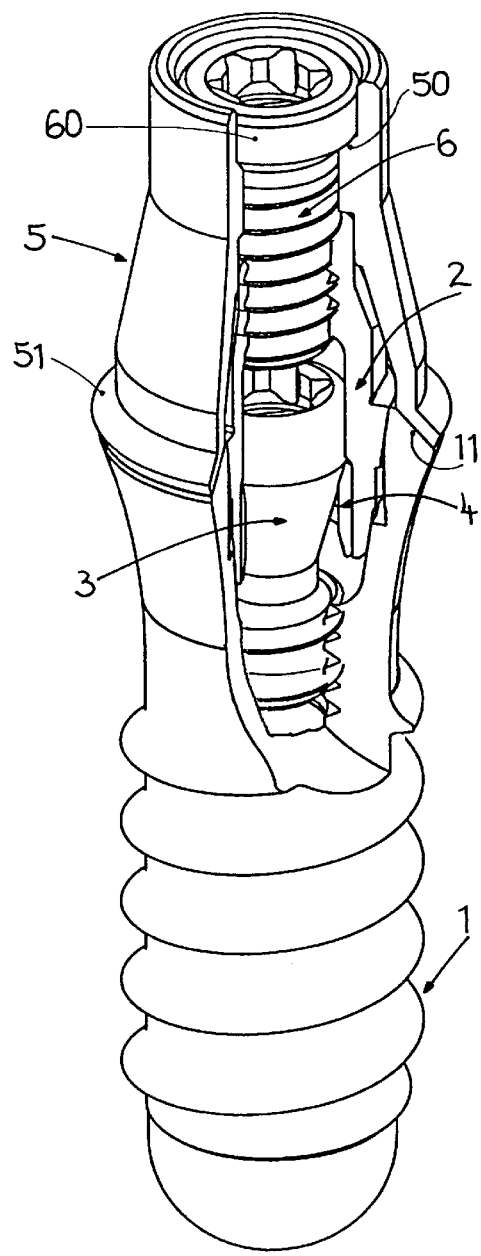
Fig. 6A
Fig. 6B

CONNECTION BETWEEN A DENTAL IMPLANT AND AN ABUTMENT

FIELD OF APPLICATION OF THE INVENTION

The present invention relates to a connection arrangement which comprises a dental implant known per se, which can be inserted into the jaw bone, and an abutment to be fixed on the implant. At the top, on the head of the implant, an axial, downwardly extending receiving hole, which is preferably widened conically upward, opens out within an encircling implant shoulder. The lower root part of the abutment, which, when there is a conical inner configuration of the receiving hole, has a complementary conical outer contour, can be inserted into the receiving hole. For the reproducible positioning of the abutment, a non-rotationally-symmetrical receiving contour may be advantageously provided in the receiving hole and have relating to it a corresponding, non-rotationally-symmetrical outer mating contour on the root part of the abutment. The non-rotationally-symmetrical contours complementing one another likewise represent a rotational securement for the inserted abutment, the rotational securement in fact already being brought about by the cone-cone connection between the inner cone of the implant and the conical root part on the abutment.

From the bottom of the receiving hole there extends further downward a coaxial. internally threaded hole for the engagement of a base screw disposed axially in the abutment, so that the abutment is fixed on the implant by screwing in of the base screw. The base screw is introduced into the abutment, the head of the base screw being supported in the abutment, while the threaded shank of the base screw protrudes out of the abutment at the bottom and engages in the internally threaded hole in the implant. Connection arrangements of this type are used both for straight abutments and for angled abutments. The base screw secures the abutment axially on the implant and—if the implant and abutment have non-rotationally-symmetrical contours engaging in one another—also against rotation in addition to the cone-cone connection. The selectable rotational positions in which the abutment can be fixed are limited by the shaping of the non-rotationally-symmetrical contours, for example the number of corners of polygons used.

PRIOR ART

The basic structure of the implant—but still without a non-rotationally-symmetrical receiving contour, preferably an internal polygon—is known for example from the monograph by SCHROEDER/SUTTER/BUSER/KREKELER: Oral Implantology, Georg Thieme Verlag Stuttgart, 2nd edition 1996, page 127. Such an implant has the implant head at the top and the shank part at the bottom, the implant head terminating at the very top with the radially encircling implant shoulder and it being possible, depending on the type of implant, for there to be an external thread on the shank part. The implant shoulder surrounds the mouth of the receiving hole conically narrowing axially downward, whereby the inner cone is produced. At the bottom of the hole, the receiving hole merges into a coaxial internally threaded hole of reduced diameter, which extends apically into the shank part and has the internal thread.

WO 94/09717 and WO 97/14371 disclose implants of the type described above which have within the receiving hole an internal polygon arranged at a distance from the implant shoulder. Complementing this, there are external polygons on the respective abutments. The internal polygon in the implant brings with it considerable advantages as a positioning aid for the reproducible positioning of the inserted abutment in conjunction with the superstructures which are adapted by the prosthetist or dental technician, and possibly as rotational securement. The angle of rotation with respect to the longitudinal axis of an inserted abutment whose neck part protruding above the implant shoulder is not rotationally symmetrical must be transferred to a dental model in relation to the anatomy surrounding the implantation site. In the case of the implant according to U.S. Pat. No. 4,960,381, the internal polygon is additionally used beforehand for screwing into the bone, in that a socket wrench is inserted into the internal polygon.

WO 97/14371 discloses a connection arrangement between an implant with an internal polygon in the conical receiving hole and an abutment with a corresponding, apically extending root part. In the case of this design, there is in the root part of the abutment, close to the lower outlet of the passage, a radial groove for receiving a spreading ring. The spreading ring is pushed onto the shank piece of the base screw and comes to lie under the screw head. The base screw can then be pushed with the screw head first into the root part, until the spreading ring slides into the radial groove. The abutment preassembled to this extent with the base screw and the spreading ring is inserted into the receiving hole of the implant. In the case of a straight abutment, the passage is axial. In the case of an angled abutment, the passage is likewise angled and may have an additional vertically oriented lateral opening for the perpendicular insertion of the screwing implement. The screwing implement is inserted through the passage or the lateral opening and the threaded shank of the base screw is thus screwed into the internally threaded hole of the implant. The screw head of the base screw presses on the spreading ring, which introduces the tensile force into the abutment, so that the latter is drawn into the receiving hole.

The connection arrangement according to WO 97/14371 has the major advantage that the screw head of the base screw does not have to be introduced from above into the passage of the abutment. This allows the passage at the coronal end, in which an internal thread for an occlusal screw may be provided, to be shaped such that it is dimensioned smaller than the diameter of the screw head of the base screw. The space available on the superstructure, for example on the artificial tooth crown, limits the size of the insertable occlusal screw. In the interests of the strength of the screw connection, however, a base screw which is not reduced in diameter in relation to the occlusal screw but has the same diameter may be used. The main resultant advantage is that screws of the same diameter as the base screw and as the occlusal screw that can be screwed into the coronal end can be used; i.e. the internally threaded hole in the implant and the internally threaded hole in the coronal part of the abutment have the same diameter. This serves for the reliability of the screw connections and simplifies the system which forms the implants of various configuration with the variety of structural parts and the set of implements.

With the connection arrangement according to WO 97/14371, significant progress was achieved in comparison with the previously applicable state of the art. The forming of the internal radial groove in the abutment and the use of the spreading ring disposed on the base screw and received in the radial groove cannot, however, be regarded as the ultimate, complete solution. The mechanical working of the radial groove in the abutment and a radial groove on the shank of the base screw in which the spreading ring is seated during the pushing of the base screw into the abutment must take place with high precision and altogether requires a not inconsiderable outlay in terms of working and inspection. Bearing in mind the relatively small dimensions of the connection arrangement, the relatively high forces to be absorbed under alternating loading and the enormous requirements for reliability, there is the need to retain the basic advantages of the connection arrangement but to lower the production outlay and, in particular, further increase the reliability. The head of the base screw presses on the relatively narrow annular surface at the top of the spreading ring and the spreading ring is for its part seated in a pressing manner on a likewise narrow horizontal annular surface within the radial groove.

OBJECT OF THE INVENTION

In view of the need to improve the functional reliability of the previously known connection arrangement and at the same time lower the production outlay, the invention is based on the object of proposing a perfected connection arrangement. A connection arrangement between an implant and a straight or angled abutment that is distinguished by extremely high reliability is to be provided. The abutment must at the same time allow itself to be fixed in a practical way on the implant and must not be loosened even as a result of micro-movements. Moreover, the connection arrangement is to comprise a small number of uncomplicated parts and consequently be inexpensive to produce. The parts of the connection arrangement should have a system character and consequently be able to be used for different variants of the connection arrangement—i.e. for combination with various abutments. The main advantages of a connection arrangement where the base screw is inserted with the screw head first into the root part of the abutment are to be retained. An additional objective here is that the flexurally greatly stressed base screw should have a small longitudinal force and a loosening moment that is as high as possible.

SUMMARY OF THE INVENTION

Provided in the abutment is an inlet, which could be an axial passage. From the side of the root part, a base screw can be pushed with its screw head first into this inlet, as far as a head zone. The threaded shank of the base screw, which is reduced in diameter with respect to the screw head and, in the inserted state, protrudes from the root part of the abutment, is intended for engagement in the axially extending internally threaded hole in the implant. After insertion of the base screw into the abutment, a support ring is pushed over the threaded shank of the base screw into the mouth of the inlet and is fixed in its intended position. Fixing takes place by radial welding to the lower edge of the abutment. An alternative possibility is for the support ring to be adhesively bonded to the inner wall of the abutment, for which purpose a biocompatible and officially approved cement or adhesive is used. A further alternative for the fixing of an inserted support ring is to provide that the lower edge of the abutment is extended in order to bend said lower edge around inward after the pushing in of the support ring, i.e. gripping under the lower edge of the support ring. The base screw then rests in each case on the fixed support ring.

It has proven to be favorable to provide the support ring on its upper and lower edges with an internal beveled surface and to shape the part of the screw neck situated beneath the screw head such that it widens conically toward the screw head. Consequently, in the screwed state, a sloping surface of the screw neck presses against the internal beveled surface of the support ring. With the support ring having an identical contour at the upper and lower edges, it does not matter which edge of the support ring is at the top. To give it elasticity, the support ring could have a penetrating vertical slit or partial slits. In a special configuration, the support ring has an internal thread complementing the threaded shank of the base screw, so that the support ring must be screwed on when it is fitted onto the base screw.

The connection arrangement comprising the abutment with the inserted base screw, which is held by the introduced support ring, and the implant is put together in the following way. The abutment is brought with the threaded shank of the base screw first up to the receiving hole of the implant, so that the threaded shank is above the internally threaded hole of the implant. If there is a non-rotationally-symmetrical receiving contour—for example an internal polygon—in the implant and a complementary outer mating contour on the abutment, it must be ensured that the two contours are in a congruent position when they are brought into place. A suitable screwing implement is used to reach through the penetrating axial passage in the abutment or a provided lateral opening into the engagement contour of the base screw and screw the latter into the internally threaded hole. Consequently, the abutment is drawn increasingly deeper and more firmly into the receiving hole, the screw neck pressing onto the support ring fixed in the abutment.

Then the further superstructure can be fitted onto the abutment, the method by which it is fastened depending on the design of the abutment respectively used. If the abutment has an internally threaded hole, a method which comes into consideration is a screw connection with an occlusal screw, which is advantageously of the same diameter as the base screw. In the anterior tooth area, or if the implant is in a slanted position, where occlusal screw connection is not possible, an abutment with a lateral hole will be used for the transversal screw connection of the fitted-on crown cap. In the case of solid abutments, the superstructure is cemented onto the abutment.

The invention is responsible for providing a connection arrangement between an implant and an abutment which is distinguished by very high functional reliability—i.e. being held together in a stable and precise manner in the fitted state—and advantageous fitting and removal properties. The connection arrangement according to the invention can be produced at efficient production costs and is suitable in particular for implants with a non-rotationally-symmetrical receiving contour in combination with straight or angled abutments with a corresponding non-rotationally-symmetrical outer mating contour.

BRIEF DESCRIPTION OF THE ATTACHED DRAWINGS

In the drawings:

FIG. 2C shows the abutment according to FIG. 2B from below as a perspective view;

FIG. 2D shows the abutment according to FIG. 2B, with offsetting of the external octagon at the root part by 22.50°, from below as a perspective view;

FIG. 2E shows a straight abutment of a third embodiment with an external octagon at the root part, a conical neck part and two lateral openings;

FIG. 3A shows a base screw of a first embodiment with a conically constricted neck;

FIG. 6A shows a connection arrangement with the implant according to FIG. 1, the abutment according to FIG. 2A, the support ring according to FIG. 4A and the base screw according to FIG. 3B as a partial section;

FIG. 6B shows the connection arrangement according to FIG. 6A with a fitted on gold cap and occlusal screw as a partial section;

EXEMPLARY EMBODIMENTS

Figure 1:
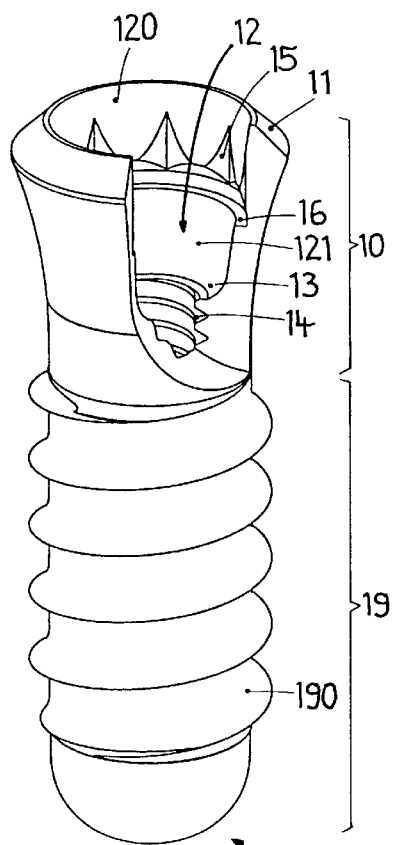
FIG. 1 shows an implant with an internal octagon in the implant head as a partial section.

The detailed description of exemplary embodiments of the connection arrangement according to the invention on the basis of the attached drawings follows.

The following statement applies to the entire further description. If reference numerals are included in a figure for the purpose of elucidating the drawing, but are not explained in the directly associated text of the description, you are referred to where they are mentioned in the descriptions of previous figures. In the interests of overall clarity, components are not usually denoted again in the subsequent figures, provided that it is clear from the drawing that they are "recurrent" components.

FIG. 1

The implant 1 used in the connection arrangement is of a construction known per se. The implant 1 has at the top the implant head 10 and at the bottom the shank part 19, the implant head 10 terminating at the very top with the radially encircling implant shoulder 11 and it being possible, depending on the type of implant, for there to be an external thread 190 on the shank part 19. The implant shoulder 11 surrounds the mouth of the receiving hole 12, conically narrowing axially downward. At the bottom 13 of the hole, the receiving hole 12 merges into a coaxial internally threaded hole 14 of reduced diameter, which extends into the shank part 19.

Formed inside the receiving hole 12 as a non-rotationally-symmetrical receiving contour there is here, by way of example, a radially encircling internal octagon 15. Beneath the internal octagon 15 lies a circular annular groove 16, which is recommendable for the machining of the internal octagon 15. The internal octagon 15 finishes in the upward direction in parabolic tips. The internal octagon 15 preferably lies within the receiving hole 12 in such a way that uninterrupted, mutually aligned cone portions 120,121 of the receiving hole 12 are retained beneath it. The implant 1 represented is a solid-screw implant; however, the connection arrangement may equally be constructed with a hollow-screw, hollow-body and solid-body implant of a straight or angled version.

FIG. 2A

This straight abutment 2 of a first embodiment has at the top the neck part 20 and the downwardly adjoining root part 29, which is conical in certain portions. Said root part is intended for insertion into the receiving hole 12 of the implant 1, while the neck part 20 protrudes above the implant shoulder 11. The neck part 20 is divided into three segments, to be specific the polygonal segment 21 directly adjoining the root part 29—here an external octagon—, the cylindrical guiding segment 23 at the very top and the cone segment 22 lying between the polygonal segment 21 and the guiding segment 23. The polygonal segment 21 is useful for reproducible positioning when taking impressions and making models and also for possible rotational securement of the fitted-on superstructure. The guiding segment 23 contributes to the centering and guiding of the fitted-on crown cap.

On the root part 29 there is a mating contour complementing the receiving contour 15 in the implant 1, consequently here an external octagon 28. Above the external octagon 28 lies a cone portion 270, which is adjacent to the polygonal segment 21, and beneath the external octagon 28 lies the cone portion 271, with which the abutment 2 ends at the lower edge 272. The two cone portions 270,271 are in alignment with one another, so that in the inserted state the upper and lower cone portions 120,270;121,271 respectively of the implant 1 and of the abutment 2 come to lie against one another. The plane faces of the polygonal segment 21 and of the external octagon 28 are preferably in alignment with one another.

Through the abutment 2 there extends an inlet 24, here in the form of an axial passage, which is divided into a plurality of zones. In the region of the guiding segment and cone segment 23, 22, an internal thread 240 is provided for receiving an occlusal screw. The internal thread 240 preferably has the same diameter as the internally threaded hole 14 in the implant 1. Beneath the internal thread 240 there lies, after a shoulder surface 244, a head zone 241, which is widened in diameter with respect to the internal thread 240 and extends approximately over the region of the polygonal segment 21 and upper cone portion 270. With a circular shoulder surface 242, the head zone 241 merges downward toward the mouth of the inlet 24 into a radial widening, i.e., widened portion 243. The widening 243 has a greater internal diameter than the head zone 241 and is intended for receiving a support ring, the depth of insertion of which is limited by the shoulder surface 242.

FIGS. 2B AND 2C

The abutment 2 represented, of a second embodiment, has in comparison with the first embodiment a modified neck part 20, which obliquely adjoins the unchanged root part 29 and, toward the free, upper end, is conically tapered as a whole. At the bottom, the abutment 2 ends with the lower edge 272. The inlet 24 is now angled, again being provided internally with the internal thread 240 and—all not visible— the head zone 241, the shoulder surface 242 and the widening 243. For the engagement of a screwing implement, the abutment 2 has on the neck part 20 a perpendicularly oriented lateral opening 200. The external octagon 28 on the root part 29 is aligned in such a way that two mutually parallel plane faces 280 of the external octagon 28 are aligned perpendicularly with respect to the inclination of the neck part 20. For better adaptation to the respective anatomical situation, various inclinations, for example 150 and 200, may be provided within a system.

FIG. 2D

Figure 2A:
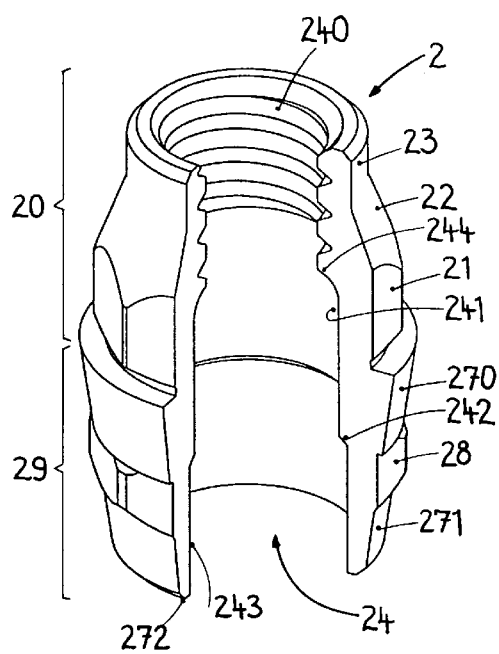
FIG. 2A shows a straight abutment of a first configuration with an external octagon at the root part and an external octagon at the neck part as a partial section.
Figure 2B:
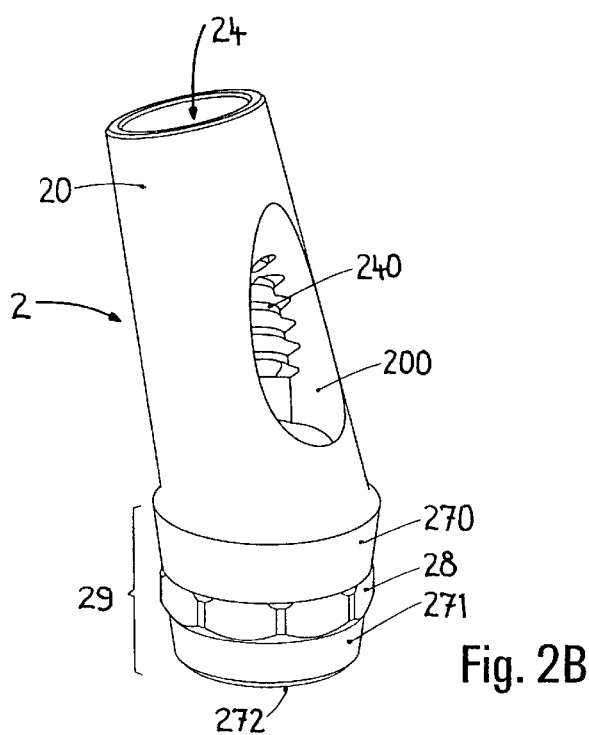
FIG. 2B shows an angled abutment of a second embodiment with an external octagon at the root part, a conical neck part and a lateral opening.
Figure 3B:
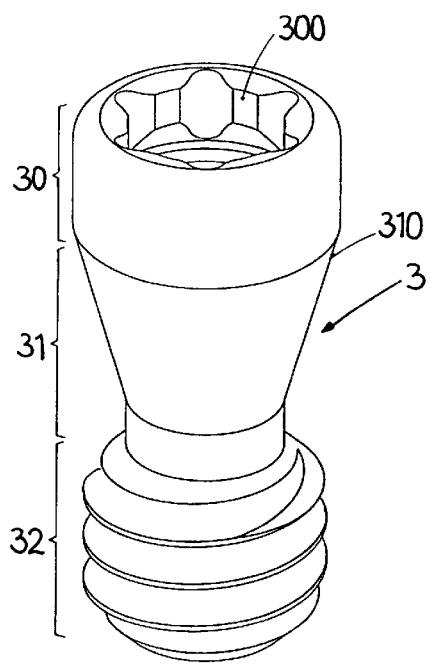
FIG. 3B shows the base screw of a second embodiment with a conically cylindrical neck.

In a variant of the angled abutment 2, the external octagon 28 has at the root part 29 an offset of 22.5°, so that all the plane faces 280 of the external octagon 28 are aligned peripherally with respect to the inclination of the neck part 20. The tips formed by the point of intersection of two neighboring plane faces 280 then lie perpendicularly with respect to the inclination of the neck part 20. With the two variants according to FIGS. 2C and 2D, 16 rotational positions respectively with an offset of 22.5° are then available.

FIG. 2E

The abutment 2 of the third embodiment has a conical neck part 20, which adjoins the unchanged root part 29 in a straight manner and advantageously terminates at the very top with a cylindrical guiding segment 23. On the neck part 20 there are two lateral openings 201 for transversal screw connection with a fitted-on crown cap. The lateral openings 201 are preferably offset from alignment with respect to one another by 22.5°. Consequently, 16 rotational positions of a transversal cap 7 fitted onto the implant 1 and the abutment 2 are available (see FIG. 6C). This makes better adaptation to the anatomical conditions encountered possible, which is relevant in particular when replacing an individual tooth.

FIG. 3A

For the construction of the connection arrangement according to the invention on the implant 1, alternatively one of the embodiments described above of the abutment 2—the neck part 20 could have further modifications—and a base screw 3 are required. Considered in the downward direction, the base screw 3 comprises the basically cylindrical screw head 30, the conically constricted screw neck 31 adjoining it and the lower threaded shank 32. Provided on the upper side of the screw head 30 is an engagement contour 300 for the screwing implement. The screw neck 31, which is conical at the top, continues steplessly beneath the screw head 30 with an initially tapering sloping surface 310 and then, in a constricted form, merges into the threaded shank 32, in a thickening form. The harmonious transitions between the screw head 30, screw neck 31 and threaded shank 32 serve for reducing concentrations of stress. In the interests of a lowest possible longitudinal screw force of the base screw 3, the surface of the threaded shank 32 should be relatively smooth and, to achieve a high loosening moment, the sloping surface 310 on the other hand should be made rougher.

FIG. 3B

The only difference from the base screw 3 described above of the first embodiment is in the geometry of the screw neck 31, which here in the second embodiment is conical-cylindrical. The sloping surface 310 in turn follows on beneath the screw head 30 without any step. The transitions are advantageously rounded.

FIGS. 4A TO 4D

Figure 4A:
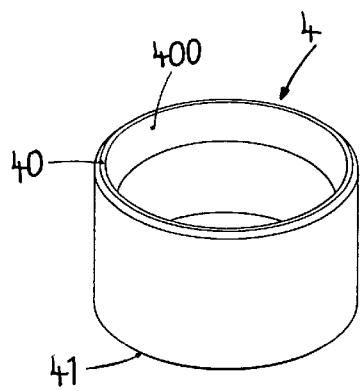
FIG. 4A shows a support ring of a first embodiment.
Figure 4B:
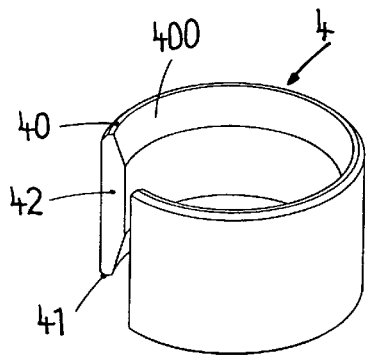
FIG. 4B shows a support ring of a second embodiment with a penetrating vertical slit.
Figure 4C:
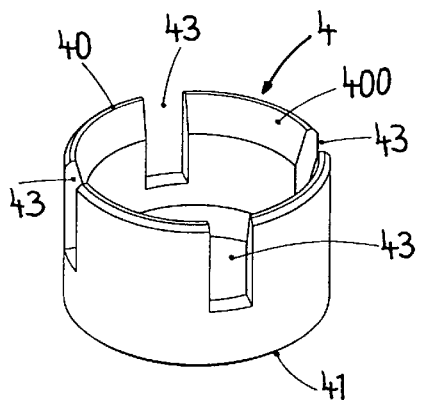
FIG. 4C shows a support ring of a third embodiment with four expansion slits.
Figure 4D:
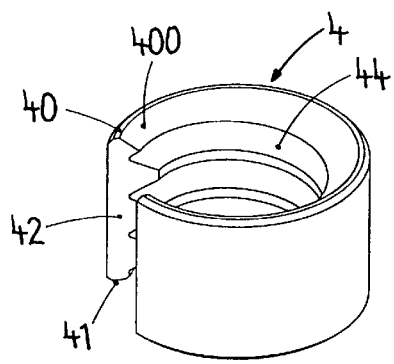
FIG. 4D shows a support ring of a fourth embodiment with an internal thread and a penetrating vertical slit.

In the first, simplest form (FIG. 4A), the support ring 4 comprises a tubular neck piece and has at its upper edge 40 an internal beveled surface 400 for providing support for the sloping surface 310 of the base screw 3. The lower edge 41 is preferably also provided with a beveled surface 400, so that during production the support ring 4 can be inserted into the abutment 2 without it mattering with which edge 40,41 first the support ring 4 is introduced. In the case of the second embodiment (FIG. 4B), the support ring 4 has a penetrating vertical slit 42 and is consequently open. In the third embodiment (FIG. 4C), a plurality of systematically distributed expansion slits 43 are provided. These expansion slits 43 run from the upper edge 40 vertically toward the lower edge 41 and extend over part of the height of the support ring 4. The beveled surface 400 is consequently repeatedly interrupted by the expansion slits 43. In the case of the fourth embodiment (FIG. 4D), the support ring 4 is open as a result of a vertical slit 42, and an internal thread 44 passes through the support ring 4. The internal thread 44 matches the thread on the threaded shank 32, so that, during preassembly, the support ring 4 can be screwed onto the base screw 3 by means of the threaded shank 32. This form of the support ring 4 is more complex to produce, but a widened beveled surface 400 is thereby obtained for the supported base screw 3.

FIG. 5A

A base screw 3, which is held by a support ring 4, is inserted into a straight abutment 2, having a polygonal segment 21, cone segment 22 and guiding segment 23, as a structural unit. Two largely similar working methods seem appropriate for the assembly of this structural unit.

First Working Method

1st step: Introduction of the screw head 30 of the base screw 3 from below into the inlet 24 of the abutment 2, so that the screw head 30 comes to lie inside the head zone 241.

2nd step: Guiding of the support ring 4 over the threaded shank 32 and insertion of the support ring 4 into the widening 243 in the abutment 2. The support ring 4 and the widening 243 together form a press fit in the upper portion.

3rd step: Fixing of the support ring 4, seated in the widening 243, by adhesively bonding or cementing in place on the widening 243 or welding at its lower edge 41 to the lower edge 272 of the abutment 2. The sloping surface 310 of the base screw 3 rests on the internal beveled surface 400 in the support ring 4.

Second Working Method

1st step: Guiding of the support ring 4 over the threaded shank 32 of the base screw 3.

2nd step: Introduction of the screw head 30 of the base screw 3 from below into the inlet 24 of the abutment 2 and insertion of the support ring 4 into the widening 243 in the abutment 2.

3rd step: Fixing of the support ring 4 seated in the widening 243.

The structural unit can be sold in this preassembled combination of the abutment 2 and base screw 3 held by the support ring 4.

Figures 5A, 5B:
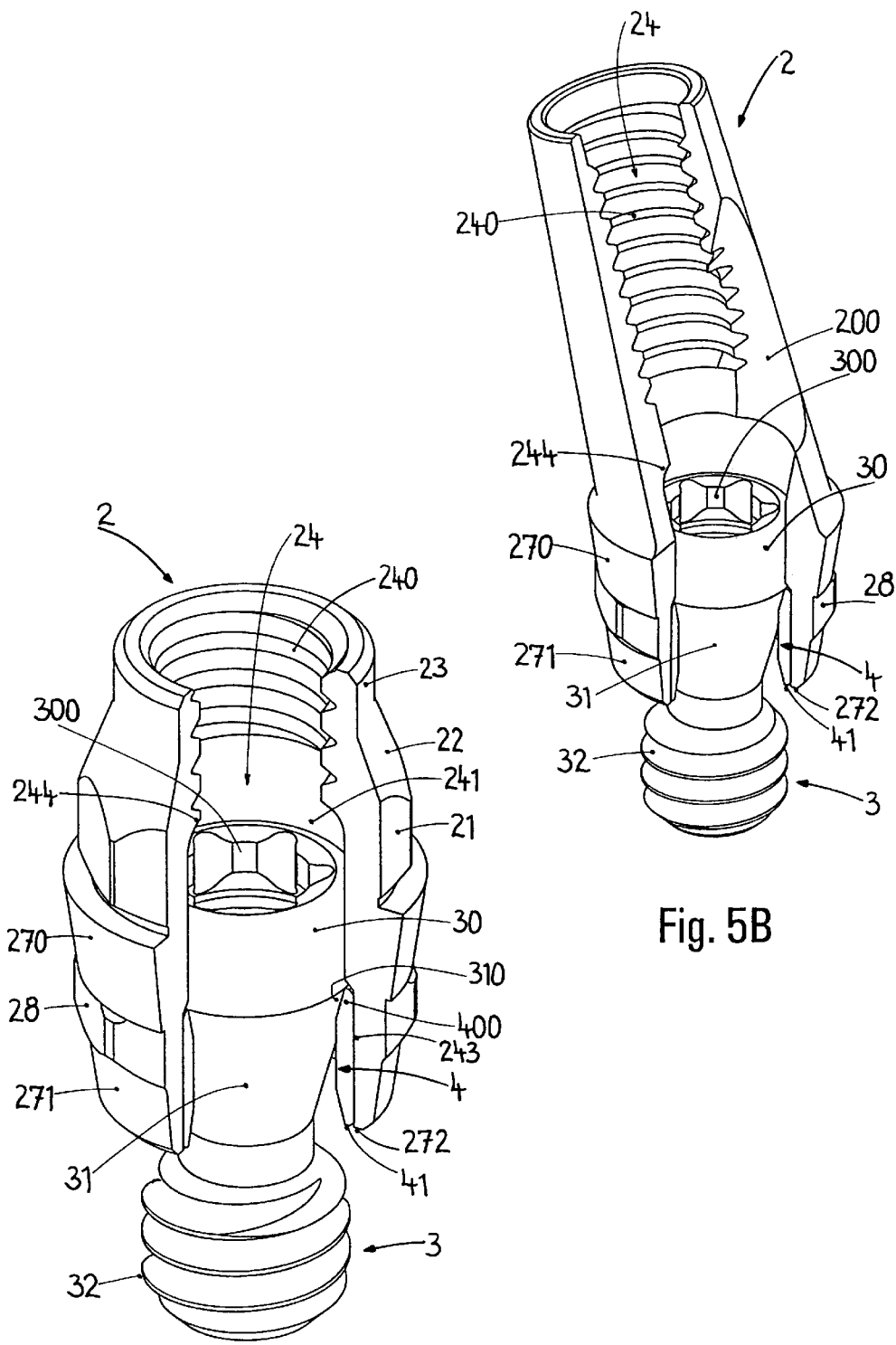
FIG. 5A shows the abutment according to FIG. 2A, the support ring according to FIG. 4A and the base screw according to FIG. 3B in combination as a partial section.
FIG. 5B shows the abutment according to FIG. 2B, the support ring according to FIG. 4A and the base screw according to FIG. 3B in combination as a partial section.
Figures 5C, 6C:
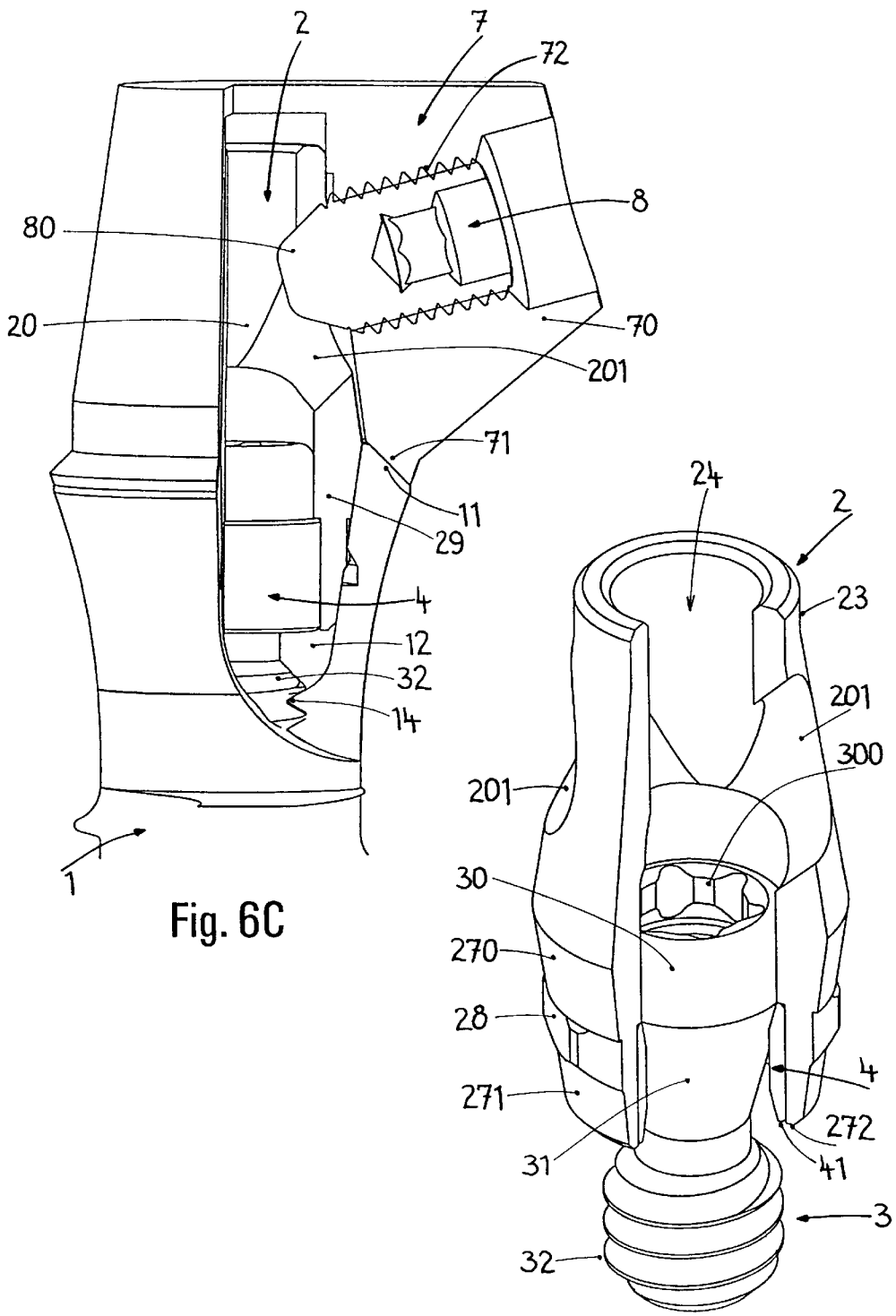
FIG. 5C shows the abutment according to FIG. 2E, the support ring according to FIG. 4A and the base screw according to FIG. 3B in combination as a partial section.
FIG. 6C shows a connection arrangement with the implant according to FIG. 1, the abutment according to FIG. 2E, the support ring according to FIG. 4A, the base screw according to FIG. 3B and a screw-connected transversal cap as a partial section.

FIGS. 5B and 5C

In the same way, a structural unit can be produced from an angled abutment 2 with the lateral opening 200 or a straight abutment 2 for transversal screw connection with the lateral openings 201 and the base screws 3 held by the support rings 4.

FIG. 6A

In the completed connection arrangement, the root part 29 of the abutment 2 is seated in the receiving hole 12 of the implant 1, while the neck part 20 of the abutment 2 protrudes above the implant shoulder 11. The base screw 3 has been screwed with its threaded shank 32 into the internally threaded hole 14 of the implant 1 and the sloping surface 310 of the base screw 3 presses on the beveled surface 400 of the support ring 4 seated firmly in the abutment 2. The forces acting on the support ring 4 via the sloping surface 310 and the beveled surface 400 have the effect that major force components are directed transversely onto the support ring 4 or the abutment 2, so that the fastening of the support ring 4 is not subjected as much to being pressed out axially. This is significant in particular if the fixing of the support ring 4 in the abutment 2 is realized by welding its lower edge 41 to the lower edge 272 of the abutment 2. In this way, the weld seam is relieved of the axial forces acting. The shoulder surface 244 is positioned such that it bounds the head zone 241 in such a way that, when the base screw 3 is unscrewed, its screw head 30 bears with its upper end face against the shoulder surface 244, before the threaded shank 32 of the base screw 3 fully disengages from the internal thread 14 in the implant 1. As a result, when the base screw 3 is unscrewed further, the abutment 2 is ejected from the cone portions 120,121 in the implant 1.

FIG. 6B

Here, the connection arrangement according to the previous figure is supplemented by a sleeve-shaped crown cap 5, known per se, which has been fitted onto the abutment 2 and is held by a conventional occlusal screw 6, engaging in the internal thread 240 in the abutment 2. The occbusal screw 6 and base screw 3 are of the same cross-sectional dimension. The screw head 60 of the occiusal screw 6 lies in a screw seat 50, which is located at the top internally in the crown cap 5. For supporting on the implant shoulder 11, the crown cap 5 has a flange-like rim 51 complementing t he implant shoulder 11.

FIG. 6C

This connection arrangement comprises an implant 1, an abutment 2 and a transversal cap 7, known per se, which has been fitted onto the abutment 2 and screw-connected transversely to the abutment 2 by means of a conventional clamping screw 8. The root part 29 of the abutment 2 is in turn seated in the receiving hole 12 of the implant 1 and the neck part 20 of the abutment 2 protrudes above the implant shoulder 11. The threaded shank 32 of the base screw 3 engages in the internally threaded hole 14 of the implant 1, the base screw 3 pressing in the way described above the beveled surface 400 of the support ring 4 seated in the abutment 2. At the very bottom of the transversal cap 7 there is a conical supporting surface 71 and a lug 70 protruding away laterally, with a transversal threaded hole 72, into which a clamping screw 8 has been screwed. The clamping screw 8 is directed at one of the two lateral openings 201, so that the tip 80 of the clamping screw protrudes into the lateral opening 201, is supported at the top against the lateral openings 201 and, as a result, presses the transversal cap 7 with the supporting surface 71 onto the implant shoulder 11.

FIGS. 7A AND 7B

Shown here is a further embodiment for the fixing of the support ring 4 inserted into the straight abutment 2, on the beveled surface 400 of which ring the sloping surface 310 of the screw neck 31 of the base screw 3 is seated. The screw head 30 is in turn located in the internal head zone 241 in the abutment 2. The initially not yet fixed support ring 4 lies in the widening 243 within the inlet 24. The abutment 2 is provided with an axially lower-lying lower edge 272', which protrudes as bending zone 273' apically in the downward direction beyond the lower edge 41 of the, to this extent positioned, support ring 4. With regard to the two alternative working methods, for the 1st and 2nd working steps of the preassembly of the base screw 3 and support ring 4 you are referred to the description relating to FIG. 5A.

To enhance the flow behavior of the bending zone 273' during the bending-around operation and to achieve optimum contouring after the bending-around operation, the bending zone 273' has an outer, radially encircling narrowing, i.e., narrowed portion, 274' with respect to the wall of the abutment 2 lying above the narrowing 274'. The transition into the narrowing 274' is formed by a concave curvature 275' and the lower edge 272' has an inwardly facing, apically open conical surface 276'.

FIGS. 7C AND 7D

Figure 7A:
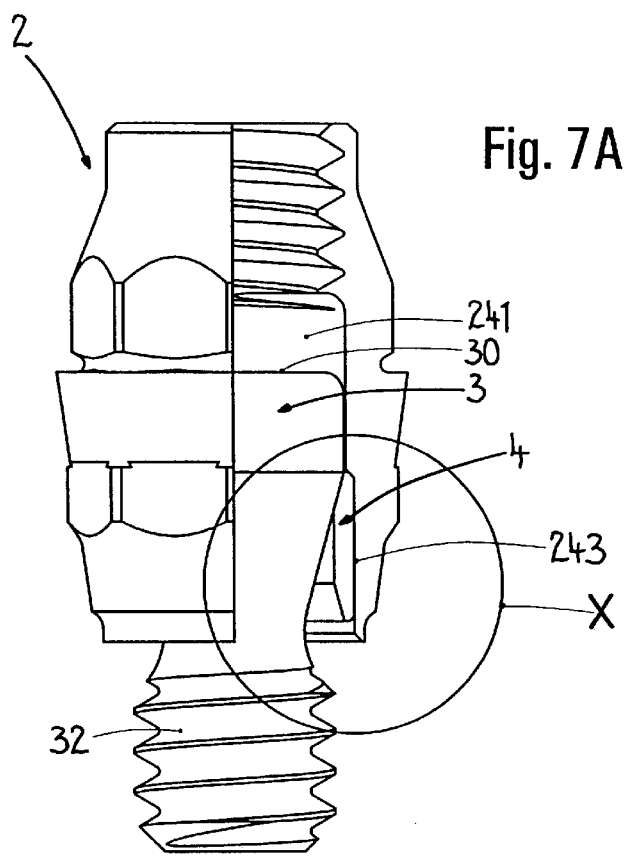
FIG. 7A shows the straight abutment according to FIG. 2A with an axially extended lower edge, inserted support ring according to FIG. 4A and inserted base screw according to FIG. 3A as a partial section.
Figure 7B:
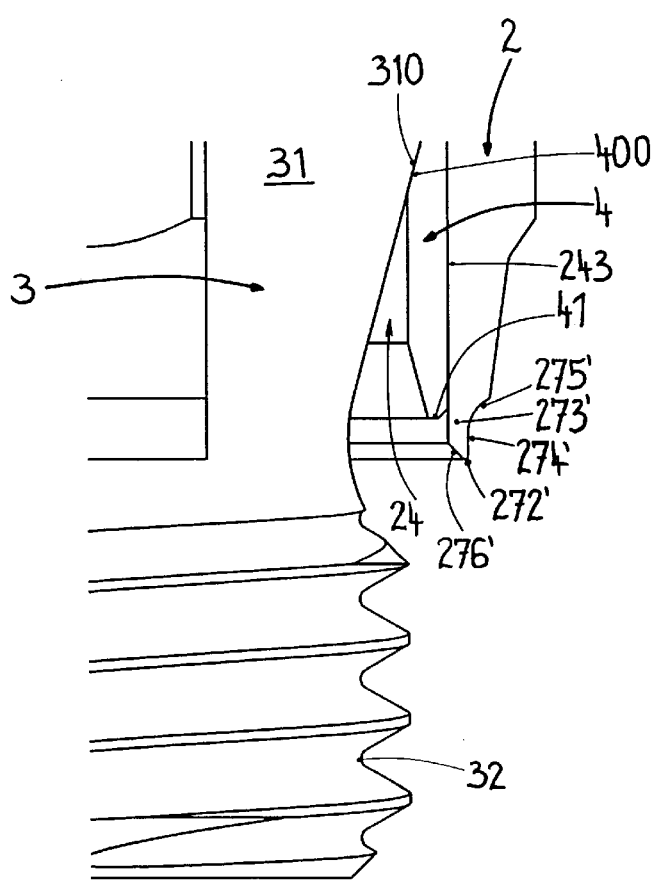
FIG. 7B shows the detail X from FIG. 7A as an enlargement.
Figure 7C:
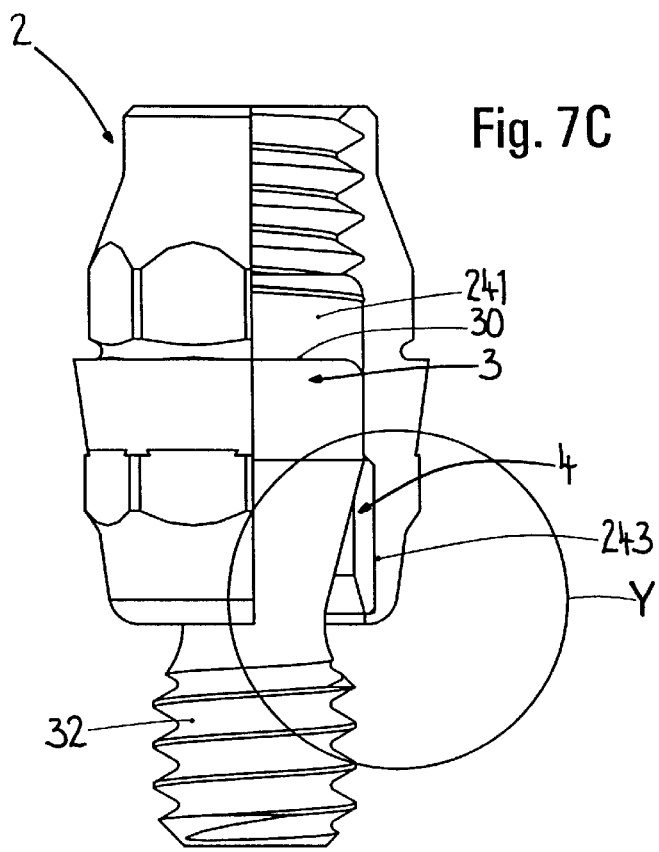
FIG. 7C shows the arrangement according to FIG. 7A with the lower edge bent around, fixing the support ring.
Figure 7D:
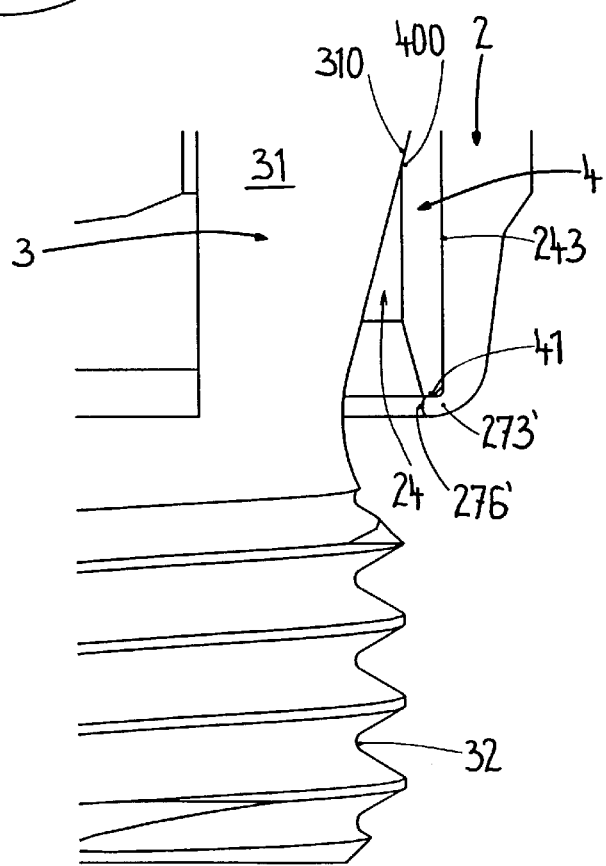
FIG. 7D shows the detail Y from FIG. 7C as an enlargement.

In the case of the arrangement formed and preassembled according to FIGS. 7A and 7B, for the permanent fixing of the support ring 4, the extended lower edge 272' is bent around in the inward-facing direction, i.e. in the direction of the screw neck 31. After the bending-around operation, the deformed bending zone 273' of the abutment 2 grips under the lower edge 41 of the support ring 4, so that the latter is now fixed in its seating in the widening 243. The narrowing 274' of the bending zone 273' now provides a rounding, running harmoniously under the support ring 4, and the previous conical surface 276' provides an axially extending edge. The base screw 3 rests on the fixed support ring 4, i.e. the configuration of the sloping surface 310 on the screw neck, which presses on the beveled surface 400 at the upper edge 40 of the support ring 4 when the base screw 3 is tightened, causes the force to be introduced essentially laterally into the abutment 2. Remaining axial force components act on the bent-around lower edge 272' to a relatively slight extent.

In the case of this embodiment of the connection arrangement, there is no need for the apparatus for laser welding and the corresponding specific inspection outlay, which can be replaced by a mechanical bending-around device with adequate quality control.

Further structural modifications can be realized with respect to the exemplary embodiments described above. The following are expressly mentioned here:

The receiving hole 12 in the implant 1 could be of a cylindrical form. It is possible to dispense with the internal octagon 15 and its positioning within the receiving hole 12 is freely selectable.

In principle, the abutment 2 must have a root part 29 complementing the receiving hole 12 of the implant 1. If the implant 1 has an internal octagon 15, abutments 2 with and without an external octagon 28 can be used in it.

The outer contour of the neck part 20 of the abutment 2 may be fully conical or fully cylindrical or have combinations of conical and cylindrical segments.

The polygonal segment 21 on the abutment 2 could be replaced by some other non-rotationally-symmetrical outer contour, which may lie at the very top of the abutment 2 or between two segments of the neck part 20. In further alternatives, the non-rotationally-symmetrical outer contour could extend—for example as a flattening—over a plurality of segments of the neck part 20 or over the entire neck part 20.

The internal thread 240 in the abutment 2 may also have a smaller or slightly larger diameter than the internal thread 14 in the implant 1.

For a person skilled in the art, it goes without saying that the inner contour of the crown cap 5 and of the transversal cap 7 must be adapted to a modified outer contour of the abutment 2 and of the implant shoulder 11.

I claim:

1. A connection arrangement comprising a dental implant (1) and an abutment (2) fixed thereon, in which the implant (1) has an implant head (10) and a downwardly extending shank part (19); provided in the implant head (10) is a receiving hole (12), having a top which opens out, and having a bottom (13), from which extends an axial, downwardly facing internally threaded blind hole (14); the abutment (2) has an upper neck part (20) and a lower root part (29), which ends at a lower edge (272), and the neck part (20) protrudes out of the implant (1), while the root part (29) is positioned in the receiving hole (12); a base screw (3), connecting the abutment (2) to the implant (1) is provided, having a screw head (30), and a threaded shank (32); the abutment (2) has an inlet (24), which begins at a lower edge (272) and a support ring (4) is positioned therein, the base screw (3) protruding through the inlet (24); wherein the abutment (2) has in the inlet (24) a widened portion (243), starting at the lower edge (272) and extending internally into the abutment (2) upwardly to a shoulder surface (242), wherein the support ring (4) is firmly inserted in the inlet (24); and the base screw (3), held in the inlet (24) of the abutment (2), rests on the support ring (4).

2. The connection arrangement as claimed in claim 1, wherein the support ring (4) has an upper edge (40) and a lower edge (41); and the lower edge (41) of the support ring (4) is welded to the lower edge (272) of the abutment (2).

3. The connection arrangement as claimed in claim 2, wherein the support ring (4) has at the upper edge (40) a radially encircling beveled surface (400), which widens conically toward the upper edge (40); the base screw (3) has a downwardly tapering sloping surface (310) above the threaded shank (32); the sloping surface (310) of the base screw (3) rests on the beveled surface (400) of the support ring (4); and the screw head (30) has an engagement contour (300) for the placing of a screwing implement.

4. The connection arrangement as claimed in claim 3, wherein the support ring (4) includes at the lower edge (41), a radially encircling beveled surface (400), which widens conically toward the lower edge (41), whereby the support ring (4) is of the same design at the upper and lower edges (40,41).

5. The connection arrangement as claimed in claim 3 or 4, wherein the support ring (4) has an internal thread (44), which complements the threaded shank (32) of the base screw (3) whereby the support ring (4) is screwed onto the base screw (3) via the threaded shank (32).

6. The connection arrangement as claimed in claim 3, wherein the base screw (3) has a screw neck (31) between its screw head (30) and threaded shank (32); the sloping surface (310) on the screw neck (31) is located near the screw head (30); the screw neck (31) is conically constricted, the screw neck (31) widening conically toward the screw head (30); and the sloping surface (310) having greater roughness than the threaded shank (32), thereby achieving a substantial loosening moment within the connection arrangement for the base screw (3).

7. The connection arrangement as claimed in claim 3, wherein the support ring (4) includes at the lower edge (41), a radially encircling beveled surface (400), which widens conically toward the lower edge (41), whereby the support ring (4) is of the same design at the upper and lower edges (40,41), and a penetrating vertical slit (42).

8. The connection arrangement as claimed in claim 3, wherein the support ring (4) includes at the lower edge (41), a radially encircling beveled surface (400), which widens conically toward the lower edge (41), whereby the support ring (4) is of the same design at the upper and lower edges (40,41), and partially cut-in expansion slits (43).

9. The connection arrangement as claimed in claim 3, wherein the base screw (3) has a screw neck (31) between its screw head (30) and threaded shank (32); the sloping surface (310) on the screw neck (31) is located near the screw head (30); the screw neck (31) is conically cylindrical, the screw neck (31) widening conically toward the screw head (30); and the sloping surface (310) having greater roughness than the threaded shank (32), thereby achieving a substantial loosening moment within the connection arrangement for the base screw (3).

10. The connection arrangement as claimed in claim 1, wherein the support ring (4) has an upper edge (40) and a lower edge (41); the abutment (2) has an apically extending bending zone (273') which extends axially beneath the lower edge (41) of the inserted support ring (4) and terminates at its bottom with a lower edge (272'); and when the bending zone (273') is bent around the lower edge (41) of the support ring (4), it grips around and under the lower edge (41) of the support ring (4).

11. The connection arrangement as claimed in claim 10, wherein, the bending zone (273') has an outer, radially encircling narrowed portion (274') relative to the wall of the abutment (2) which is located above the narrowed portion (274'); the transition into the narrowed portion (274') is formed by a concave curvature (275'); and the lower edge (272') has an inwardly facing, apically open conical surface (276'), thereby achieving enhanced flow behavior of the bending zone (273') and optimum contouring after the bending zone (273') is bent around the lower edge (41) of the support ring (4).

12. The connection arrangement as claimed in claim 1, wherein the neck part (20) of the abutment (2) adjoins the root part (29) of the abutment (2) in a straight form; the inlet (24) passes through the abutment (2) and allows a screwing implement to be used to reach into the base screw (3) from the side of the neck part (20).

13. The connection arrangement as claimed in claim 12, wherein the neck part (20) of the abutment (2) for a superstructure (7) which is adapted to be transversally connected, has a first and a second transversally oriented lateral opening (201); and the second lateral opening (201) is offset in relation to the first lateral opening (201) by approximately 22.5°.

14. The connection arrangement as claimed in claim 1, wherein the neck part (20) of the abutment (2) has an internal thread (240) for the engagement of an occlusal screw (6) for the fixing of a superstructure (5); and the internally threaded hole (14) in the implant (1) and the internal thread (240) in the neck part (20) of the abutment (2) are of the same diameter.

15. The connection arrangement as claimed in claim 1, wherein the receiving hole (12) in the implant (1) widens conically upward and has a non-rotationally-symmetrical receiving contour (15); and the root part (29) has an outer conical part (270,271) that is complementary to the conical receiving hole (12) and an outer mating contour (28) that is complementary to the receiving contour (15) in the implant (1).

16. The connection arrangement as claimed in claim 15, wherein the non-rotationally-symmetrical receiving contour (15) on the implant (1) is an internal polygon (15), above which there is an uninterrupted cone portion (120) and beneath which there is another uninterrupted cone portion (121), the two cone portions (120,121) being in alignment with one another; the outer conical part (270,271) includes two cone portions (270,271) and the mating contour (28) on the abutment (2) is an external polygon (28), above which one cone portion (270) is positioned and below which the other cone portion (271) is positioned, the two cone portions (270,271) being in alignment with one another.

17. The connection arrangement as claimed in claim 16, wherein; the widened portion (243) has a greater clear diameter than a head zone (241) positioned above it in the abutment (2), which receives the screw head (30) of the inserted base screw (3); together with the support ring (4), the widened portion (243) forms a press fit, in the upper portion, in the coronal direction; the head zone (241) has a greater clear diameter than the region of the inlet (24) remaining above it; and the head zone (241) ends in the upward direction at a constricting shoulder surface (244), which is positioned in a defined manner, whereby, when the base screw (3) is unscrewed, its screw head (30) bears with its upper end face against the shoulder surface (244), before the threaded shank (32) of the base screw (3) fully disengages from the internal thread (14) in the implant (1), and, when the base screw (3) is unscrewed further, the abutment (2) is ejected from the cone portions (120,121) in the implant (1).

18. The connection arrangement as claimed in claim 12 or 15, wherein in the implant (1), the receiving contour (15) is an internal octagon (15); on the root part (29) of the abutment (2), the complementary mating contour (28) is an external octagon (28) with eight plane faces (280); on an abutment (2) with a neck part (20) adjoining the root part (29) in an angled manner, the external octagon (28) is positioned such that two plane faces (280) which are parallel and opposite one another are each perpendicular to the inclination of the neck part (20).

19. The connection arrangement as claimed in claim 12 or 15, wherein in the implant (1), the receiving contour (15) is an internal octagon (15); on the root part (29) of the abutment (2), the complementary mating contour (28) is an external octagon (28) with eight plane faces (280); and on an abutment (2) with a neck part (20) adjoining the root part (29) in an angled manner, the external octagon (28) is positioned such that the external octagon (28) is offset by 22.5°, whereby the edges formed at the point of intersection of two neighboring plane faces (280) are inclined at the same angle as the root Part (29) with respect to the neck part (20).

20. The connection arrangement as claimed in claim 1, wherein on the neck part (20) of the abutment (2) there is an outer polygonal segment (21) having plane faces each of which are at least in substantial alignment with corresponding plane faces of the external octagon (28) on the root part (29).

21. The connection arrangement as claimed in claim 20, wherein the polygonal segment (21) is an external octagon (21) adjacent to the root part (29); an upwardly tapering cone segment (22) is above the polygonal segment (21); and a terminating cylindrical guiding segment (23) is above the cone segment (22).

22. The connection arrangement as claimed in claim 1, wherein the neck part (20) of the abutment (2) adjoins the root part (29) of the abutment (2) in an angled form; and the neck part (20) has a vertically oriented lateral opening (200) to allow a screwing implement to be used to reach into the base screw (3).

23. The connection arrangement as claimed in claim 1, wherein the abutment (2) is adapted for use with a superstructure (7) and is screwed on transversally, the neck part (20) having at least one transversally oriented lateral opening (201) to allow a screwing implement to be used to reach into the base screw (3).

24. The connection arrangement as claimed in claim 1, wherein the widened portion (243) extends uninterrupted internally into the abutment (2) upwardly to the shoulder surface (242).

25. An abutment (2) with a base screw (3) and support ring (4) for the fixing of a dental implant (1) having a receiving hole (12) and an internally threaded hole (14), comprising an upper neck part (20); and a lower root part (29), which ends at a lower edge (272), an inlet (24) beginning at the lower edge (272); the base screw (3) having: a screw head (30), and a threaded shank (32), for engaging with the internally threaded hole (14) in the implant (1); wherein the abutment (2) has in the inlet (24) a widened portion (243), starting at the lower edge (272) and extending internally into the abutment (2) upwardly to a shoulder surface (242), the support ring (4) being positioned in the inlet (24); and the base screw (3) protruding through the support ring (4), wherein the support ring (4) is firmly inserted in the inlet (24), and the base screw (3), rests on the support ring (4).

26. The abutment (2) as claimed in claim 25, wherein the support ring (4) has an upper edge (40) and a lower edge (41); and the lower edge (41) of the support ring (4) is welded to the lower edge (272) of the abutment (2).

27. The abutment (2) as claimed in claim 26, wherein the support ring (4) has at the upper edge (40) a radially encircling beveled surface (400), which widens conically toward the upper edge (40); The base screw (3) has a downwardly tapering sloping surface (310), above the threaded shank (32); the sloping surface (310) of the base screw (3) rests on the beveled surface (400) of the support ring (4); and the screw head (30) has an engagement contour (300) for the placing of a screwing implement.

28. The abutment (2) as claimed in claim 27, wherein the support ring (4) includes at the lower edge (41), a radially encircling beveled surface (400), which widens conically toward the lower edge (41), whereby the support ring (4) is of the same design at the upper and lower edges (40,41).

29. The abutment (2) as claimed in claim 27 or 28, wherein the support ring (4) has an internal thread (44), which complements the threaded shank (32) of the base screw (3) whereby the support ring (4) is screwed onto the base screw (3) via the threaded shank (32).

30. The abutment (2) as claimed in claim 27, wherein the base screw (3) has a screw neck (31) between its screw head (30) and threaded shank (32); the sloping surface (310) on the screw neck (31) is located near the screw head (30); the screw neck (31) is conically constricted, the screw neck (31) widening conically toward the screw head (30); and the sloping surface (310) having greater roughness than the threaded shank (32), thereby achieving a substantial loosening moment within the connection arrangement for the base screw (3).

31. The abutment (2) as claimed in claim 27, wherein the support ring (4) includes at the lower edge (41), a radically encircling beveled surface (400), which widens conically toward the lower edge (41), whereby the support ring (4) is of the same design at the upper and lower edges (40,41), and a penetrating vertical slit (42).

32. The abutment (2) as claimed in claim 27, wherein the support ring (4) includes at the lower edge (41) a radially encircling beveled surface (400), which widens conically toward the lower edge (41), whereby the support ring (4) is of the same design at the upper and lower edges (40,41), and partially cut-in expansion slits (43).

33. The abutment (2) as claimed in claim 27, wherein the base screw (3) has a screw neck (31) between its screw head (30) and threaded shank (32); the sloping surface (310) on the screw neck (31) is located near the screw head (30); the screw neck (31) is conically cylindrical, the screw neck (31) widening conically toward the screw head (30); and the sloping surface (310) having greater roughness than the threaded shank (32), thereby achieving a substantial loosening moment within the connection arrangement for the base screw (3).

34. The abutment (2) as claimed in claim 25, wherein the support ring (4) has an upper edge (40) and a lower edge (41); the abutment (2) has an apically extending bending zone (273') which extends axially beneath the lower edge (41) of the inserted support ring (4) and terminates at its bottom with a lower edge (272'); and when the bending zone (273') is bent around the lower edge (41) of the support ring (4), it grips around and under the lower edge (41) of the support ring (4).

35. The abutment (2) as claimed in claim 34, wherein, the bending zone (273') has an outer, radially encircling narrowed portion (274') relative to the wall of the abutment (2) which is located above the narrowed portion (274'); the transition into the narrowed portion (274') is formed by a concave curvature (275'); and the lower edge (272') has an inwardly facing, apically open conical surface (276'), thereby achieving enhanced flow behavior of the bending zone (273') and optimum contouring after the bending zone (273') is bent around the lower edge (41) of the support ring (4).

36. The abutment (2) as claimed in claim 25, wherein the neck part (20) of the abutment (2) adjoins the root part (29) of the abutment (2) in a straight form; the inlet (24) passes through the abutment (2) and allows a screwing implement to be used to reach into the base screw (3) from the side of the neck part (20).

37. The abutment (2) as claimed in claim 36, wherein in the case of an abutment (2) for a superstructure (7) which is adapted to be transversally screw-connected, the neck part (20) has a first and a second transversally oriented lateral opening (201); and the second lateral opening (201) is offset in relation to the first lateral opening (201) by approximately 22.5°.

38. The abutment (2) as claimed in claim 25, wherein the neck part (20) of the abutment (2) has an internal thread (240) for the engagement of an occlusal screw (6) for the fixing of a superstructure (5); and the internal thread (240) in the neck part (20) is of the same diameter as the internally threaded hole (14) in the implant (1).

39. The abutment (2) as claimed in claim 25, wherein the root part (29) of the abutment (2) has an outer conical part (270,271) and an outer mating contour (28), the conical part (270,271) complementing the receiving hole (12) widening conically upward in the implant (1); and the outer mating contour (28) complementing a non-rotationally-symmetrical receiving contour (15) provided in the receiving hole (12).

40. The abutment (2) as claimed in claim 39, wherein the outer conical part (270,271) includes two cone portions (270,271) and the mating contour (28) on the abutment (2) is an external octagon (28), above which one cone portion (270) is positioned and below which the other cone portion (271) is positioned, the two cone portions (270,271) being in alignment with one another.

41. The abutment (2) as claimed in claim 40, wherein the widened portion (243) has a greater clear diameter than a head zone (241) positio above it in the abutment (2), which receives the screw head (30) of the inserted base screw (3); together with the support ring (4), the widened portion (243) forms a press fit, in the upper portion, in the coronal direction; the head zone (241) has a greater clear diameter than the region of the inlet (24) remaining above it; and the head zone (241) ends in the upward direction at a constricting shoulder surface (244), which is positioned in a defined manner, whereby, when the base screw (3) is unscrewed, its screw head (30) bears with its upper end face against the shoulder surface (244), before the threaded shank (32) of the base screw (3) fully disengages from the internal thread (14) in the implant (1), and, when the base screw (3) is unscrewed further, the abutment (2) is ejected from the cone portions (120,121) in the implant (1).

42. The abutment (2) as claimed in claim 36 or 39, wherein on the root part (29) of the abutment (2), the complementary mating contour (28) is an external octagon (28) with eight plane faces (280); on an abutment (2) with a neck part (20) adjoining the root part (29) in an angled manner, the external octagon (28) is positioned such that two plane faces (280) which are parallel and opposite one another are each perpendicular to the inclination of the neck part (20).

43. The abutment (2) as claimed in claim 36 or 39, wherein on the root part (29) of the abutment (2), the complementary mating contour (28) is an external octagon (28) with eight plane faces (280); and on an abutment (2) with a neck part (20) adjoining the root part (29) in an angled manner, the external octagon (28) is positioned such that the external octagon (28) is offset by 22.5°, whereby the edges formed at the point of intersection of two neighboring plane faces (280) are inclined at the same angle as the root part (29) with respect to the neck part (20).

44. The abutment (2) as claimed in claim 25, wherein on the neck part (20) of the abutment (2) there is an outer polygonal segment (21) having a plane faces each of which are at least in substantial alignment with corresponding plane faces of the external octagon (28) on the root part (29).

45. The abutment (2) as claimed in claim 44, wherein the polygonal segment (21) is an external octagon (21) adjacent to the root part (29); an upwardly tapering cone segment (22) is above the polygonal segment (21); and a terminating cylindrical guiding segment (23) is above the cone segment (22).

46. The abutment (2) as claimed in claim 25, wherein the neck part (20) of the abutment (2) adjoins the root part (29) of the abutment (2) in an angled form; the neck part (20) has a vertically oriented lateral opening (200) to allow a screwing implement to be used to reach into the base screw (3).

47. The abutment (2) as claimed in claim 25, wherein the abutment (2) is adapted for use with a superstructure (7) and is screwed on transversally, the neck part (20) having at least one transversally oriented lateral opening (201) to allow a screwing implement to be used to reach into the base screw (3).

48. A method for manufacturing an abutment (2) for connection to an implant (1), comprising the steps:

providing an abutment (2) having a receiving hole (12) and an internally threaded hole (14), said abutment comprising further an upper neck part (20) and a, lower root part (29), which ends at a lower edge (272);

providing a base screw (3), said base screw comprising a screw head (30) and a threaded shank (32);

arranging a support ring (4) at said base screw (3) between said screw head (30) and said threaded shank (32);

inserting said base screw (3) and said support ring (4) firmly into in a widened portion (243) of an inlet (24) of said lower root part (29), said widened portion (243) beginning at said lower edge (272) of said inlet (24) and extending internally upward as far as a shoulder surface (242); and fixing said support ring (4) in said widened portion (243).

49. An abutment (2) with a base screw (3) and support ring (4) for the fixing of a dental implant (1) having a receiving hole (12) and an internally threaded hole (14), comprising an upper neck part (20) and a lower root part (29), which ends at a lower edge (272), an inlet (24) beginning at the lower edge (272);

the base screw (3) having:

a screw head (30) and a threaded shank (32), for engaging with the internally threaded hole (14) in the implant (1);

the support ring (4) being positioned in the inlet (24) and the base screw (3) protruding through the support ring (4), the support ring (4) being firmly inserted into the inlet (24), and the base screw (3) rests on the support ring (4);

wherein the support ring (4) has a lower edge (41), said lower edge (41) is welded to the lower edge (272) of the abutment (2).

50. An abutment (2) with a base screw (3) and support ring (4) for the fixing of a dental implant (1) having a receiving hole (12) and an internally threaded hole (14), comprising an upper neck part (20) and a lower root part (29), which ends at a lower edge (272), an inlet (24) beginning at the lower edge (272);

the base screw (3) having:

a screw head (30) and a threaded shank (32), for engaging with the internally threaded hole (14) in the implant (1);

the support ring (4) being positioned in the inlet (24); and the base screw (3) protruding through the support ring (4), the support ring (4) being firmly inserted into the inlet (24), and the base screw (3) rests on the support ring (4);

wherein the abutment (2) has an apically extending bending zone (273') which extends axially beneath a lower edge (41) of the support ring (4) and terminates at its bottom with a lower edge (272'), said the bending zone (273') is bent around said lower edge (41) and grips around and under the lower edge (41) of the support ring (4).

\* \* \* \* \*